(12) United States Patent
Mitchell et al.

(10) Patent No.: US 11,357,713 B2
(45) Date of Patent: Jun. 14, 2022

(54) ANTIMICROBIAL COMPOSITION

(71) Applicant: Conopco, Inc., Englewood Cliffs, NJ (US)

(72) Inventors: Deidre Lee Mitchell, Oxford, CT (US); Luis Roberto Misso, Miami, FL (US); Bijan Harichian, Irvine, CA (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/743,011

(22) PCT Filed: Jun. 13, 2016

(86) PCT No.: PCT/EP2016/063517
§ 371 (c)(1),
(2) Date: Jan. 9, 2018

(87) PCT Pub. No.: WO2017/008974
PCT Pub. Date: Jan. 19, 2017

(65) Prior Publication Data
US 2018/0228706 A1 Aug. 16, 2018

(30) Foreign Application Priority Data
Jul. 14, 2015 (EP) .................................... 15176699

(51) Int. Cl.
A61K 8/35 (2006.01)
A61Q 17/00 (2006.01)
A01N 25/04 (2006.01)
A61K 8/34 (2006.01)
A61K 8/40 (2006.01)
A01N 37/28 (2006.01)
A01N 31/14 (2006.01)
A01N 35/04 (2006.01)
A61K 8/42 (2006.01)
A61K 8/49 (2006.01)

(52) U.S. Cl.
CPC ............... A61K 8/34 (2013.01); A01N 25/04 (2013.01); A01N 31/14 (2013.01); A01N 35/04 (2013.01); A01N 37/28 (2013.01); A61K 8/347 (2013.01); A61K 8/35 (2013.01); A61K 8/40 (2013.01); A61K 8/42 (2013.01); A61K 8/4913 (2013.01); A61Q 17/005 (2013.01)

(58) Field of Classification Search
None
See application file for complete search history.

(56) References Cited

U.S. PATENT DOCUMENTS

| 3,976,495 | A | 8/1976 | Buckman et al. |
| 5,443,820 | A | 8/1995 | Holderbaum et al. |
| 5,981,073 | A | 11/1999 | Pickett et al. |
| 8,834,856 | B2 * | 9/2014 | Spaulding ................ A61K 8/34 424/59 |
| 9,181,161 | B2 * | 11/2015 | Rudolph ............... A61K 31/185 |
| 2001/0028888 | A1 | 10/2001 | Heidenfelder et al. |
| 2003/0082464 | A1 | 5/2003 | Takashima et al. |
| 2004/0009200 | A1 | 1/2004 | Seyler et al. |
| 2006/0002872 | A1 | 1/2006 | Candau et al. |
| 2006/0002873 | A1 | 1/2006 | Candau |
| 2006/0083698 | A1 | 4/2006 | Candau |
| 2007/0140997 | A1 | 6/2007 | Candau et al. |
| 2008/0038213 | A1 | 2/2008 | Carola et al. |
| 2009/0143489 | A1 * | 6/2009 | Winn .................... A61K 8/345 514/785 |
| 2011/0268676 | A1 | 11/2011 | Winn |
| 2014/0335029 | A1 * | 11/2014 | Rudolph ............... A01N 37/36 424/55 |
| 2015/0118165 | A1 | 4/2015 | Rudolph et al. |
| 2015/0118172 | A1 | 4/2015 | Rudolph et al. |
| 2016/0015031 | A1 * | 1/2016 | Pesaro .................... A61K 8/35 424/65 |

FOREIGN PATENT DOCUMENTS

| CN | 104010525 | | 8/2014 |
| CN | 104271109 | | 1/2015 |
| DE | 4107439 | | 9/1992 |
| DE | 4107489 | | 9/1992 |
| EP | 2774481 | | 9/2014 |
| FR | 2918560 | | 1/2009 |
| GB | 1581443 | | 12/1980 |
| KR | 20130061229 | A * | 6/2013 |
| KR | 20130061229 | M * | 6/2013 |
| WO | WO0056279 | | 9/2000 |
| WO | WO02083781 | | 10/2002 |
| WO | WO2005030856 | | 4/2005 |
| WO | WO-2006-029818 | * | 3/2006 |
| WO | WO2006029818 | | 3/2006 |
| WO | WO2007111157 | | 10/2007 |
| WO | WO2007133508 | | 11/2007 |
| WO | WO20008024738 | | 2/2008 |
| WO | WO2009074409 | | 6/2009 |
| WO | WO2009080427 | | 7/2009 |

(Continued)

OTHER PUBLICATIONS

Baldwin et al (Emerging Infectious Diseases, www.cdc.gov/eid, 13(3), 2007, 458-461). (Year: 2007).*

(Continued)

Primary Examiner — Celeste A Roney
(74) Attorney, Agent, or Firm — Stephanie S. DelPonte

(57) ABSTRACT

An antimicrobial composition with a synergistic combination of ingredients is described. Cosmetic compositions containing the antimicrobial composition with improved preservation properties are also described. The cosmetic compositions are effective in treating the skin to cleanse, moisturize and to reduce the effects of aging and photo damage and treat other skin conditions after being topically applied.

6 Claims, No Drawings

(56) References Cited

FOREIGN PATENT DOCUMENTS

| | | |
|---|---|---|
| WO | WO2010115009 | 10/2010 |
| WO | WO2011086124 | 7/2011 |
| WO | WO2013159865 | 10/2013 |
| WO | WO2014149363 | 9/2014 |
| WO | WO2014149390 | 9/2014 |

OTHER PUBLICATIONS

IPRP2 in PCTEP2016063517, dated Nov. 10, 2017.
Search Report & Written Opinion in PCTEP2016063517, dated Jul. 20, 2016.
Search Report and Written Opinion in EP15176699, dated Sep. 23, 2015.
Written Opinion in PCTEP2016063517, dated May 30, 2017.

* cited by examiner

ANTIMICROBIAL COMPOSITION

FIELD OF THE INVENTION

The present invention is directed to an antimicrobial composition containing a synergistic blend of ingredients and also to cosmetic compositions containing the antimicrobial composition.

BACKGROUND OF THE INVENTION

Skin is subject to deterioration through dermatological disorders, environmental abuse (wind, air conditioning, central heating) or through the normal aging process (chronoaging) which may be accelerated by exposure of skin to sun (photoaging). In recent years the demand for cosmetic compositions and cosmetic methods for improving the appearance and condition of skin has grown enormously. There is a need for effective antimicrobial compositions that are compatible with such cosmetic compositions.

Consumers also frequently seek other benefits from cosmetic products in addition to their skin benefits. The concept of "sensitive skin" has also raised the consumer demand for cosmetic products which have safe and effective antimicrobial compounds.

Cosmetic and compositions for improving the condition and appearance of skin include many different antimicrobial systems.

U.S. Pat. No. 3,976,495 to Buckman et. al. issued on Aug. 24, 1976 discloses the use hydroxyacetophenone derivatives as fungicides. United States Patent Application No. 2011/0268676 to Winn published on Nov. 3, 2011 discloses the use of hydroxamic acids as preservatives for cosmetic compositions.

United States Application publication nos. US 2015/0118172 and US 2015/0118165 to Thomas Rudolph, et. al. both published on Apr. 30, 2015 and US 2014/0335029 to Thomas Rudolph et. al. published on Nov. 13, 2014 disclose the use of specific cyclohexanol(s) and cyclohexylalkanol(s) as antimicrobial agents.

There continues to be a need, however, for safe and effective antimicrobial compositions for cosmetic compositions for topical application to skin to confer various benefits including but not limited to cleansing, moisturizing, treating/delaying the visible signs of aging and photo damaged skin such as wrinkles, lines, sagging, hyperpigmentation, age spots and other skin conditions.

We have now surprisingly found that an antimicrobial composition containing a combination of i. phenyl alkanol(s) or phenyl alkoxyl compound(s) or both; ii. hydroxamic acid(s) having the structure of (RCONHOH) where R is a linear alkyl group and blends thereof; iii. one or more hydroxyacetophenone(s), and iv. one or more of cycloalkyl compounds selected from cyclohexanol(s), cycloalkanol(s), adamantanol(s), adamantanealkanol(s), amino adamantane(s), ammonium adamantane(s), norbornanol(s), norbornane alkanol(s), amino norbornane(s), ammonium norbornane(s) and blends thereof, which combination provided synergistic efficacy which is substantially greater than that conferred by either the individual compounds or a different combination in preventing the growth of numerous gram negative bacteria, gram positive bacteria, yeast and mold microorganisms including but not limited to *Burkholderia cepacia, Pseudomonas aeruginosa, Pseudomonas putida, Enterobacter gergoviae, Klebsiella* species, *Staphylococcus aureus, Candida albicans, Aspergillus brasiliensis* and others and where the inventive antimicrobial composition is additionally compatible with cosmetic skin formulations for cleansing or treating numerous skin conditions.

SUMMARY OF THE INVENTION

In a first aspect, the present invention is directed to an antimicrobial composition, including but not limited to:
  a. one or more phenyl alkanol(s) or phenyl alkoxyl(s) or a blend thereof;
  b. one or more hydroxamic acid(s) having the structure (RCONHOH) where R is linear alkyl or a blend thereof;
  c. one or more hydroxyacetophenone(s) or a blend thereof, and
  d. one or more cycloalkyl compound(s) selected from the group consisting of cyclohexanol(s), cyclohexylalkanol(s), adamantanol(s), adamantanealkanol(s), amino adamantane(s), ammonium adamantane(s), norbornanol(s), norbornane alkanol(s), amino norbornane(s), ammonium norbornane(s) or a blend thereof.

In another aspect of the invention is a cosmetic composition including but not limited to a cosmetically acceptable base formulated with the above described antimicrobial composition.

In a further aspect of the invention is a method of preventing at least one of gram negative bacteria, gram positive bacteria, yeast and mold microorganism(s) growth or any combination thereof in a cosmetic composition including but not limited to the steps of:
  a. preparing a cosmetically acceptable base and
  b. blending the base with the above described antimicrobial composition until homogenous.

In an additional aspect of the invention is a method of treating the skin with a cosmetic composition including but not limited to the step of applying to the skin the above described cosmetic composition.

All other aspects of the present invention will more readily become apparent upon considering the detailed description and examples which follow.

Skin, as used herein, is meant to include skin on the face, neck, chest, back, arms (including underarms), hands, legs, buttocks and scalp. Active, as used herein, is meant to include a component that improves a skin characteristic and/or benefits skin wherein the same can be, and preferably, is an active in a cosmetic composition, and most preferably, a cream, lotion, balm, deodorant, or gel.

Comprising, as used herein, is meant to include consisting essentially of and consisting of. For the avoidance of doubt, therefore, the cosmetic composition and method of this invention may consist essentially of or consist of the claimed components. All ranges identified herein are meant to include all ranges subsumed therein if, for example, reference to the same is not explicitly made.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight of the referenced composition unless stated otherwise.

DETAILED DESCRIPTION

In a first aspect, the present invention is directed to an antimicrobial composition including but not limited to:

a. one or more phenyl alkanol(s) or phenyl alkoxyl(s) or a blend thereof;

b. one or more hydroxamic acid(s) having the structure (RCONHOH) where R is linear alkyl or a blend thereof;

c. one or more hydroxyacetophenone(s) or a blend thereof, optionally where one or more of the hydroxyacetophenones are independently ring substituted with one, two, three or four additional hydroxyl groups; and d. one or more cycloalkyl compounds selected from the group consisting of cyclohexanol(s), cyclohexylalkanol(s), adamantanol(s), adamantanealkanol(s), amino adamantane(s), ammonium adamantane(s), norbornanol(s), norbornane alkanol(s), amino norbornane(s), ammonium norbornane(s) or a blend thereof.

Preferably the antimicrobial composition contains:

a. at least 50, preferably 60, more preferably 70, even more preferably 80, even more preferably 90, even more preferably 95, even more preferably 99 or most preferably 100%, preferably 50 to 100, more preferably 60 to 99, more preferably from 70 to 95, even more preferably 80 to 100% of the total phenyl alkanol(s) and phenyl alkoxyl(s) present are selected from phenoxyethanol, benzyl alcohol, phenethyl alcohol or a blend thereof;

b. at least 50, preferably 60, more preferably 70, even more preferably 80, even more preferably 90, even more preferably 95, even more preferably 99 or most preferably 100%, preferably 50 to 100, more preferably 60 to 99, more preferably from 70 to 95, even more preferably 80 to 100 % of the total hydroxamic acid(s) present are selected from Cl to C12 linear alkyl, preferably C6 to C12 linear alkyl, and more preferably include octanohydroxamic acid, caprohydroxamic acid, laurohydroxamic acid, hexanohydroxamic acid or a blend thereof;

c. at least 50, preferably 60, more preferably 70, even more preferably 80, even more preferably 90, even more preferably 95, even more preferably 99 or most preferably 100%, preferably 50 to 100, more preferably 60 to 99, more preferably from 70 to 95, even more preferably 80 to 100% of the total hydroxyacetophenone(s) present are selected from 4-hydroxyacetophenone, 3-hydroxyacetophenone, 2-hydroxyacetophenone or a blend thereof;

d. at least 50, preferably 60, more preferably 70, even more preferably 80, even more preferably 90, even more preferably 95, even more preferably 99 or most preferably 100%, preferably 50 to 100, more preferably 60 to 99, more preferably from 70 to 95, even more preferably 80 to 100% of the total cycloalkyl compound(s) present has the structure of I, II, III or any combination thereof:

I.

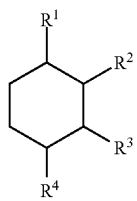

II.

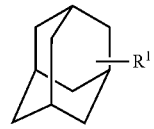

III.

where
R1=—OH, —OCH3, —OCH2CH3, —NH2, NH(CH3), —N(CH3)2, —N+(CH3)3X—(X=F, Cl, Br, I)
R2=—COOCH2CH3, —H
R3=—H, —OH, —OCH3
R4=C6H11—CH—OH; C6H11—CH—OCH3—; C6H5—CH—OCH2CH3; 4 C6H11—CH—OCH2CH3

Advantageously the antimicrobial composition contains:

a. the phenyl alkanol(s) or phenyl alkoxyl alkanol(s) or both as a total amount in a concentration of 0.1 to 25 wt. %;

b. the hydroxamic acid(s) as a total amount in a concentration of about 0.1 to 25 wt. %;

c. the hydroxyacetophenone(s) as a total amount in a concentration of about 0.1% to 25 wt. %;

d. the cycloalkyl compound(s) as a total amount in a concentration of about 0.1 to 25 wt. %; and e. a compatible carrier in a concentration of about 99.4 to 0 wt. %.

Preferably the cycloalkyl compound is selected from compounds (1) through (14) or blends thereof:

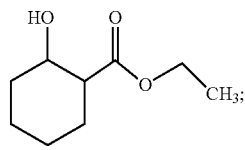

(1)

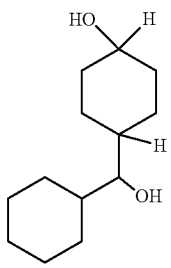

(2)

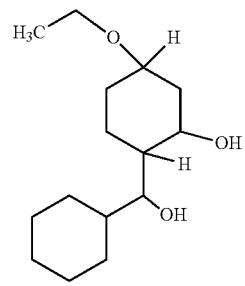

(3)

Preferably the cycloalkyl compound(s) includes compound (1), compound (3) or a blend thereof; more preferably the weight ratio of compound (1) to compound (3) is in the range of about 0.4 to 2; most preferably the weight ratio of compound (1) to compound (3) has a maximum of about 1.

In another aspect of the invention is a cosmetic composition including but not limited to:
a. a cosmetically acceptable base and
b. the above described antimicrobial composition.

Preferably the antimicrobial composition is present in the cosmetic composition in an amount effective to at least inhibit 99% of at least one viable microorganism from re-growth using the modified challenge test at day 21 wherein the microrganism is selected from *B.cepacia, P.aeruginosa, P.putida, S.aureus, C.albicans* and *A.brasiliensis* or any combination thereof.

More preferably the cosmetic composition contains:
a. the phenyl alkanol(s), phenyl alkoxyl alkanol(s) or blend thereof in a concentration as a total amount based on the cosmetic composition of about 0.2 to 1.0 wt. %; preferably at least about 0.4 wt. % and a maximum of about 0.7% wt. %;

b. the hydroxamic acid(s) in a concentration as a total amount based on the cosmetic composition of about 0.1 to 1.2 wt. %; preferably at least about 0.35 wt. % and a maximum of about 0.7% wt. %;

c. the hydroxyacetophenone(s) in a concentration as a total amount based on the cosmetic composition of about 0.1% to 1.0 wt. %; preferably at least about 0.25 wt. % and a maximum of about 0.5 wt. %.

d. the cycloalkyl compound(s) in a concentration as a total amount based on the cosmetic composition of about 0.5 to 1.0 wt. %.

Advantageously isothiazolinone antimicrobial compounds are present in the cosmetic composition at a maximum level of 0.15 wt. % as a total amount based on the weight of the cosmetic composition.

In a further aspect of the invention is a method of preventing at least one of gram negative bacteria, gram positive bacteria, yeast and mold microorganism(s) growth or any combination thereof in a cosmetic composition including but not limited to the steps of:
a. preparing a cosmetically acceptable base and
b. blending the base with the above described antimicrobial composition until homogenous.

In an additional aspect of the invention is a method of treating the skin with a cosmetic composition including but not limited to the step of applying to the skin the above described cosmetic composition.

i. Phenyl Alkanol(s) and Phenyl Alkoxyl Alkanol(s):

The inventive antimicrobial composition preferably includes one or more phenyl alkanol(s), phenyl alkoxyl alkanol(s) or blends thereof. Useful compounds include phenoxyethanol, benzyl alcohol, phenethyl alcohol, and the like.

ii. Hydroxamic Acid(s)

The inventive antimicrobial composition preferably includes one or more hydroxamic acid(s) i.e. (RCONHOH) where R is linear alkyl, preferably where R is C1 to C12, more preferably C6 to C12 linear alkyl. Useful compounds include caprohydroxamic (caprylohydroxamic) acid, octanohydroxamic acid, laurohydroxamic acid, hexanohydroxamic acid or a blend thereof and the like.

iii. Hydroxyacetophenone(s)

The inventive antimicrobial composition preferably includes one or more hydroxyacetophenone(s) optionally ring substituted with one, two, three or four additional hydroxyl groups or a blend thereof. Useful compounds include 4-hydroxyacetophenone, 3-hydroxyacetophenone, 2-hydroxyacetophenone or a blend thereof and the like.

iv. Cycloalkyl Compound(s):

The inventive antimicrobial composition preferably includes a cycloalkyl compound selected from one or more of cyclohexanol(s), cyclohexylalkanol(s), adamantanol(s), adamantane alkanol(s), amino adamantane(s), ammonium adamantane(s), norbornanol(s), norbornane alkanol(s), amino norbornane(s) or ammonium norbornane(s) or blends thereof; preferably according to structures I, II and III.

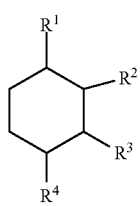
(I)

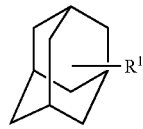
(II)

(III)

where

R1=—OH, —OCH3, —OCH2CH3, —NH2, NHCH3, —N(CH3)3, —N+(CH3)3X—(X=F, Cl, Br or I)

R2=—COOCH2CH3, —H

R3=—H, —OH, —OCH3

R4=C6H11—CH—OH; C6H11—CH—OCH3—; C6H5—CH—OCH2CH3; 4 C6H11—CH—OCH2CH3

Useful cycloalkyl compounds include the following:

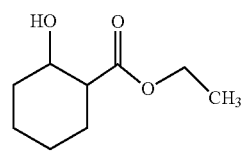
(1)

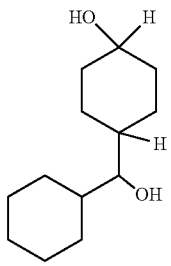
(2)

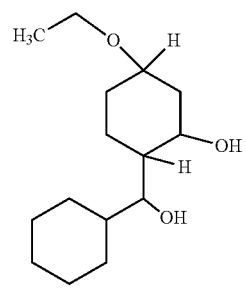
(3)

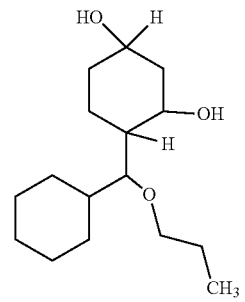
(4)

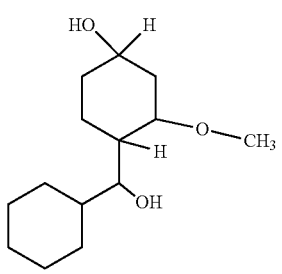
(5)
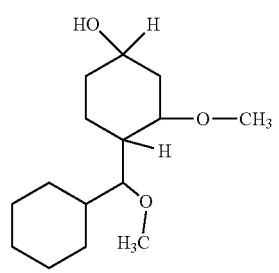
(6)
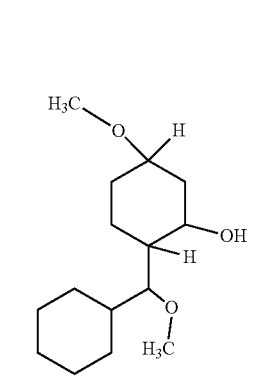
(7)
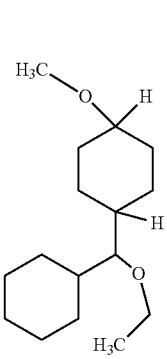
(8)
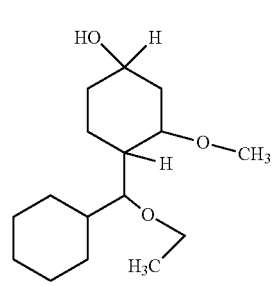
(9)
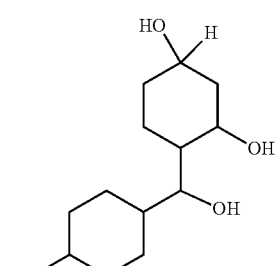
(10)
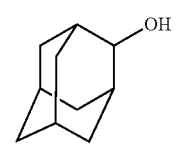
(11)
2-Adamantanol
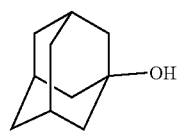
(12)
1-Adamantanol
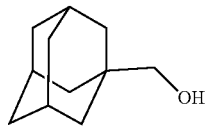
(13)
1-Adamantanemethanol
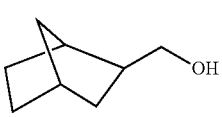
(14)
Norbornanemethanol Antimicrobial Composition Carriers:

Optionally a carrier may be used with the inventive antimicrobial composition. The carrier is preferably compatible with the ingredients of the antimicrobial composition such that it doesn't degrade its efficacy or cause any decomposition or deleterious chemical changes or promote or cause the inventive components to react or interact with the carrier or with each other to the detriment of the antimicrobial efficacy of the antimicrobial composition or negatively affect the stability, efficacy, safety or quality of a cosmetic composition to which the carrier is formulated with. The carrier may be a single compound or a blend of compounds which are used in amounts effective to solubilize or disperse the ingredients of the antimicrobial composition. Compatible is herein defined as a compound or blend of compounds that forms a solution or dispersion with the ingredients of the antimicrobial composition where the efficacy of the antimicrobial composition is maintained at greater than 99, 98, 95, 90, 80, 70 or 60 percent of its initial efficacy after storage in the dark at 45 degrees C. and 1 ATM pressure for 60 days. Initial efficacy is its efficacy as measured with the modified challenge test described below at day 21 using the most resistant organism selected from *B.cepacia, P.aeruginosa, P.putida, B.cepacia* 054, *S.aureus, C.albicans* and *A.brasiliensis;* within one hour after preparation of the inventive composition at 25 degrees C. and 1 ATM using the same carrier and the results are compared to the same modified challenge test performed on an aliquot of the same antimicrobial composition stored in the dark at 45 degrees C. and 1 ATM pressure for 60 days.

The carrier may include one or more of the cosmetically acceptable carriers described below. In addition to or in place of such cosmetically acceptable carriers, the carrier may include one or more of the following compounds: synthetic or naturally derived compounds including but not limited to linear or cyclic aliphatic, alkenyl, alkynyl and aromatic hydrocarbon(s); heterocyclic compounds, aldehydes, esters, ketones, ethers or carboxylic acids; the foregoing optionally substituted with one or more functional groups where the functional group may contain oxygen, nitrogen, sulfur, phosphorus, halogen or any combination thereof.

Antimicrobial Effectiveness:

The inventive antimicrobial composition is expected to be efficacious against at least one or more of the following microorganisms: gram negative, gram positive, yeast and mold. Preferably it is effective against at least two, three or all of them. The inventive composition was shown to be effective against the following microorganisms:

Gram negative: *B.cepacia, P.aeruginosa,* and *P.putida;*
 Gram positive: *S.aureus;* Yeast: *C.albicans* and Mold: *A.brasiliensis;* using the Modified Challenge test described below.

Cosmetic Composition:

Actives suitable for use in this invention are meant to include but not be limited to opacifiers, colorants, skin lightening agents, moisturizers, plant extracts, anti-inflammatories, surfactants, wrinkle reducing agents, mixtures thereof or the like.

Cosmetic Compositions of the present invention typically include cosmetically acceptable carrier components in addition to the inventive antimicrobial composition described herein. These may also comprise the antimicrobial carrier. Water is the most preferred carrier. Amounts of water may preferably range from about 1 to about 98%, more preferably, from about 5 to about 90%, and most preferably, from about 35 to about 80%, and optimally, from about 40 to about 80% by weight, based on total weight of the total cosmetic composition and including all ranges subsumed therein.

Cosmetically acceptable carriers suitable for use in this invention may include mineral oils, di and triglyceride oils, silicone oils, synthetic or natural esters, and alcohols. Total amounts of these materials may range from about 0.1 to about 50%, and preferably, from about 0.1 to about 30%, and most preferably, from about 1 to about 20% by weight of the cosmetic composition, including all ranges subsumed therein.

Silicone oils are divided into the volatile and non-volatile variety. The term "volatile" as used herein refers to those materials which have a measurable vapor pressure at ambient temperature (e.g. 25 C). Volatile silicone oils are preferably chosen from cyclic or linear polydimethylsiloxanes containing from about 3 to about 9, and preferably, from about 4 to about 5 silicon atoms.

Linear volatile silicone materials generally have viscosities of less than about 5 centistokes ($0.5 \times 10^{-5}$ m$^2$/s) at 25° C. while cyclic materials typically have viscosities of less than about 10 centistokes ($1.0 \times 10$-5 m$^2$/s).

Nonvolatile silicone oils useful as a carrier material in the cosmetic composition include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from about 5 to about 100,000 centistokes ($0.5 \times 10^{-5}$ to $10,000 \times 10^{-5}$ m$^2$/s) at 25° C.

Silicone oils (especially, Dimethicone 35 to 75 centistokes ($3.5 \times 10^{-5}$ to $7.5 \times 10^{-5}$ m$^2$/s)) suitable for use are often made commercially available from Dow Corning and are preferred.

Among suitable esters are:
(1) Alkenyl or alkyl esters of fatty acids having 10 to 20 carbon atoms like isopropyl palmitate, isopropyl isostearate, isononyl isonanonoate, oleyl myristate, isopropyl myristate, oleyl stearate, and oleyl oleate;
(2) Ether-esters such as fatty acid esters of ethoxylated fatty alcohols;
(3) Polyhydric alcohol esters such as ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxy-ethylene sorbitan fatty acid esters;
(4) Wax esters such as beeswax, spermaceti, myristyl myristate, stearyl stearate; and
(5) Sterol esters, of which soya sterol and cholesterol fatty acid esters are examples thereof.

Emulsifiers are preferably present in the cosmetic composition of the present invention. Total concentration of the emulsifiers may range from about 0.1 to about 40%, and preferably, from about 1 to about 20%, and most preferably, from about 1 to about 7% by weight of the cosmetic composition, including all ranges subsumed therein.

The emulsifier may be selected from the group consisting of anionic, nonionic, cationic and amphoteric actives. Particularly preferred nonionic actives are those with a $C_{10}$-$C_{20}$ fatty alcohol or acid hydrophobe condensed with from about 2 to about 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di- $C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers.

Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol as well as emulsifying/thickening additives like hydroxyethylacrylate/sodium acryloyldimethyl taurates copolymer/squalane and mixtures thereof.

Emulsion stabilizers generally classified as vegetable based liquids may also be used. Preferred stabilizers are sold under the name Oilwax LC and made available commercially by Lotioncrafter.

In addition to the antimicrobial composition of the invention, additional antimicrobial compounds can desirably be incorporated into the cosmetic compositions of this invention to protect against the growth of potentially harmful microorganisms. However, preservatives are regulated ingredients with upper limitations defined by regulatory agencies. In addition, many preservatives are skin sensitizers and it is preferable to use the lowest concentration of preservative and protect against potentially harmful microorganisms which can spoil the product and pose a consumer safety risk. Suitable traditional antimicrobial compounds for cosmetic compositions of this invention are alkyl esters of para-hydroxybenzoic acid. Other antimicrobial compounds which have more recently come into use include Isothiazolinones, DMDM hydantoin derivatives, propionate salts, and a variety of quaternary ammonium compounds. Cosmetic chemists are familiar with appropriate antimicrobial compounds and routinely choose them to satisfy the preservative challenge test and to provide product efficacy and stability. Particularly preferred antimicrobial compounds are iodopropynyl butyl carbamate, phenoxyethanol, methyl paraben, propyl paraben, imidazolidinyl urea, sodium dehydroacetate and benzyl alcohol. The antimicrobial compounds should be selected having regard for the use in the cosmetic composition and possible incompatibilities between the antimicrobial compounds and other ingredients in the emulsion. Additional antimicrobial compounds are preferably employed in amounts ranging from about 0.01% to about 1% by weight of the cosmetic composition, including all ranges subsumed therein. Most preferably Isothiazolinone antimicrobial compounds are present at a maximum level of 0.02%, 0.06% or 0.15% and preferably are absent from the inventive cosmetic composition.

Thickening agents may optionally be included in cosmetic compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes crosslinked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl Dimethyltaurate/Vinyl Pyrrolidone Copolymer. Another preferred synthetic polymer suitable for thickening is an acrylate-based polymer made commercially available by Seppic and sold under the name Simulgel INS100.

Amounts of the thickener, when used, may range from about 0.001 to about 5%, and preferably, from about 0.1 to about 3%, and most preferably, from about 0.1 to about 1.5% by weight of the cosmetic composition including all ranges subsumed therein.

Conventional humectants may be employed in the present invention. These are generally polyhydric alcohol-type materials. Typical polyhydric alcohols include glycerol (i.e., glycerine or glycerin), propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. Most preferred is glycerin, propylene glycol or a mixture thereof. The amount of humectant employed may range anywhere from 0.5 to 25%, preferably between 1 and 20% by weight of the cosmetic composition.

Fragrances, colorants, fixatives and abrasives may optionally be included in cosmetic composition of the present invention. Each of these substances may range from about 0.05 to about 5%, preferably between 0.1 and 3% by weight.

Turning to the actives suitable for use in the cosmetic compositions, the same can include opacifiers like $TiO_2$ and ZnO and colorants like iron oxide red, yellow and black. Such opacifiers and colorants typically have a particle size from 50 to 1200 nm, and preferably, from 50 to 350 nm.

To enhance skin moisturization, actives classified as cationic ammonium compounds may optionally be used in the cosmetic compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from about 0.01 to about 30%, and preferably, from about 0.1 to about 15% by weight of the cosmetic composition.

When cationic ammonium compounds are used, preferred additional active for use with the same are moisturizing agents such as substituted ureas like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-di-hydroxyethyl urea; N,N'-di-hydroxypropyl urea; N,N,N'-tri-hydroxyethyl urea; tetra(hydroxymethyl) urea; tetra(hydroxyethyl) urea; tetra (hydroxypropyl) urea; N-methyl-N'-hydroxyethyl urea; N-ethyl-N,N-N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea. The latter is available as a 50% aqueous liquid from the National Starch & Chemical Division of ICI under the trademark Hydrovance.

Amounts of substituted urea, when used, in the cosmetic composition of this invention range from about 0.01 to about 20%, and preferably, from about 0.5 to about 15%, and most preferably, from about 1 to about 10% based on total weight of the cosmetic composition and including all ranges subsumed therein.

When cationic ammonium compound and substituted urea are used, in a most especially preferred embodiment at least from about 1 to about 15% glycerin external to the particle is used, based on total weight of the cosmetic composition and including all ranges subsumed therein.

Cosmetic compositions of the present invention may include vitamins as the desired active. Illustrative vitamins are Vitamin A (retinol) as well as retinol esters like retinol palmitate and retinol propionate, Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in cosmetic compositions according to the present invention may range from 0.001 to 10%, preferably from 0.01% to 1%, optimally from 0.05 to 0.5% by weight of the cosmetic composition.

Azelaic acid, ubiquinone, dihydroxyacetone (DHA) and mixtures thereof may also be used as actives in the cosmetic composition of this invention. Such compounds, when used, typically make up from about 0.2 to 10%, and preferably, from about 0.5 to 5% by weight of the cosmetic composition, including all ranges subsumed therein.

Other optional actives suitable for use in this invention include resveratrol, resorcinols like 4-ethyl resorcinol, 4-hexyl resorcinol, 4-phenylethyl resorcinol, dimethoxytoluyl propyl resorcinol, 4-cyclopentyl resorcinol, 4-cyclohexylresorcinol, alpha-an/or beta-hydroxyacids, phenylethyl resorcinol (Symwhite 377 from Symrise), undecylenol phenylalanine (Seppi White from Seppic) mixtures thereof or the like. Such actives, when used, collectively make up from about 0.001 to about 12% by weight of the cosmetic composition.

Desquamation promoters may be present. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone compounds. Representative acids are glycolic and its derivatives, lactic and malic acids. Salicylic acid is representative of the beta-hydroxycarboxylic acids. Amounts of these materials when present may range from about 0.01 to about 15% by weight of the cosmetic composition.

A variety of herbal extracts may optionally be included as actives in cosmetic compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary. Soy extracts may be used and especially when it is desirable to include retinol.

Also optionally suitable for use include materials like chelators (e.g., EDTA), $C_{8-22}$ fatty acid substituted saccharides, lipoic acid, retinoxytrimethylsilane (available from Clariant Corp. under the Silcare 1M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Occlusives like Oilwax LC are often desired. Amounts of these materials may range from about 0.000001 to about 10%, preferably from about 0.0001 to about 3% by weight of the cosmetic composition.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the cosmetic composition of this invention is from about 4 to about 8, and preferably, from about 4.25 to about 7.75, and most preferably, from about 6 to about 7.5, including all ranges subsumed therein. The cosmetic composition of this invention may be a solid stick or bar. Viscosity of the cosmetic composition of this invention is, however, preferably from about 1,000 to about 120,000 cps, and most preferably, from about 5,000 to 80,000 cps, taken at ambient temperature NS and a shear rate of $1s^{-1}$ with a strain controlled parallel plate rheometer made commercially available from suppliers like T.A. Instruments under the Ares name.

A wide variety of packaging can be employed to store and deliver the cosmetic composition of this invention. Preferably the package should be able to contain or prevent any elevated pressure build-up during storage and use of the product. Pump dispensers configured to either prevent or withstand high pressure build-up, may be used.

Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered in a stick cosmetic composition formulation in a container with propel-repel mechanism where the stick moves on a platform towards a dispensing orifice. Metallic cans pressurized by a propellant and having a spray nozzle serve as packaging for antiperspirants, shave creams and other personal care products. Toilette bars may have packaging constituted by a cellulosic or plastic wrapper or within a cardboard box or even encompassed by a shrink wrap plastic film.

The following examples are provided to facilitate an understanding of the present invention. The examples are not intended to limit the scope of the claims.

EXAMPLE 1

Several cosmetic compositions were formulated as listed below in tables 1a to 8a according to the procedure below and their efficacy to retard the growth of specific microorganisms was assessed in corresponding tables 1b to 8b using the modified challenge method described below. Inventive and Comparative cosmetic compositions were made using inventive and comparative combinations of antimicrobial compounds.

TABLE 1a

| SF Base control - LM-16024-93 Inventive | | |
|---|---|---|
| Ingredient | Trade Name | Weight % active basis (a) |
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xanthan Gum | Keltrol CG | 0.3 |
| Potassium Hydroxide (45%) | Potassium Hydroxide | 1.0 |

TABLE 1a-continued

| SF Base control - LM-16024-93 Inventive | | |
|---|---|---|
| Ingredient | Trade Name | Weight % active basis (a) |
| Sodium Hydroxide (50%) | Sodium Hydroxide | to adjust to a pH of about 5 to 8 |
| Stearic Acid (vegetable) | Palmera B1802G | 2.4 |
| Glycerol Stearate/Stearamide AMP | Ritasynt IP | 1.4 |
| Glycerol Monostearate (vegetal) | Cutina GMS V | 0.6 |
| Cetyl Alcohol | Lanette 16-96 NF | 0.4 |
| PEG-100 Stearate | Myrj 59P/Myrj S-100 | 1.2 |
| optional additive(s) | | 8.0 |
| Dimethicone 50 CST ($5 \times 10^{-5}$ m²/S) | DC200 Fluid, 50 CST ($5 \times 10^{-5}$ m²/S) | 1.0 |
| Phenoxyethanol | Phenoxyethanol | 0.5% |
| Cycloalkyl compound (1) | | 0.425% |
| Cycloalkyl compound (3) | | 0.425% |
| Hydroxyacetophenone | SymSave H (b) | 0.25% |
| Caprylhydroxamic Acid/Propanediol | Zeastat (a) | 0.35% |

Compound 1:

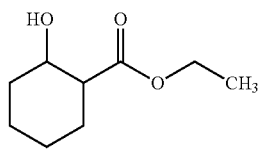

Compound 3:

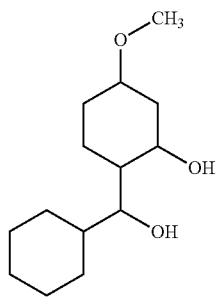

(a) Zeastat was used as obtained from Inolex located in Philadelphia, PA, USA and contains 80 to 95 wt. % propanediol and 2 to 20 wt. % caprylhydroxamic acid according to the manufacturer.
(b) SymSave H was obtained from Symrise Inc. with a location in Holzminden, Germany.

TABLE 1b

| Microbial test results | | | | | |
|---|---|---|---|---|---|
| | Log 10 cfu/g | | | | |
| | Pool 1 B. cepacia, P. aeruginosa P. putida | Pool 2 B. cepacia 054 | Pool 3 S. aureus | Pool 4 C. albicans | Pool 5 A. brasiliensis |
| Inoculum Level | 6.47 | 6.82 | 7.09 | 5.80 | 5.41 |
| Day 2 | <1.0 | <1.0 | <1.0 | 1.0 | 5.01 |
| Day 7 | <1.0 | <1.0 | <1.0 | <1.0 | <1.0 |
| Day 14 | <1.0 | <1.0 | <1.0 | <1.0 | <1.0 |
| Day 21 | <1.0 | <1.0 | <1.0 | <1.0 | <1.0 |

TABLE 2a

SF Base Control - LM-16024-78 Comparative - No Hydroxyacetophenone present

| Ingredient | Trade Name | Weight % |
|---|---|---|
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xanthan Gum | Keltrol CG | 0.3 |
| Potassium Hydroxide (45%) | Potassium Hydroxide | to adjust to a pH of about 5 to 8 |
| Stearic Acid (vegetable) | Palmera B1802G | 2.4 |
| Glycerol Stearate/Stearamide AMP | Ritasynt IP | 1.4 |
| Glycerol Monostearate (vegetal) | Cutina GMS V | 0.6 |
| Cetyl Alcohol | Lanette 16-96 NF | 0.4 |
| PEG-100 Stearate | Myrj 59P/Myrj S-100 | 1.2 |
| optional ingredients | | 9.5 |
| Dimethicone 50 CST ($5 \times 10^{-5}$ m$^2$/S) | DC200 Fluid, 50 CST ($5 \times 10^{-5}$ m$^2$/S) | 1.0 |
| Phenoxyethanol | Phenoxyethanol | 0.5 |
| Cycloalkyl compound 3 | | 0.8 |
| Caprylhydroxamic Acid/Propanediol | Zeastat | 0.7 |

TABLE 2b

Microbial Test Results

Log 10 cfu/g

| | Pool 1 B. cepacia, P. aeruginosa P. putida | Pool 2 B. cepacia 054 | Pool 3 S. aureus | Pool 4 C. albicans | Pool 5 A. brasiliensis |
|---|---|---|---|---|---|
| Inoculum Level | 6.34 | 6.89 | 7.11 | 5.61 | 5.49 |
| Day 2 | <1.0 | <1.0 | 5.79 | 4.35 | 5.34 |
| Day 7 | <1.0 | <1.0 | 3.15 | <1.0 | 4.18 |
| Day 14 | <1.0 | <1.0 | 4.13 | <1.0 | <1.0 |
| Day 21 | <1.0 | <1.0 | 2.36 | <1.0 | <1.0 |

TABLE 3a

SF Base Control - LM-16024-79 Comparative - No Hydroxyacetophenone and hydroxamic acid present

| Ingredient | Trade Name | Weight % |
|---|---|---|
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xanthan Gum | Keltrol CG | 0.3 |
| Potassium Hydroxide (45%) | Potassium Hydroxide | As needed to adjust to a pH of 5 to 8 |
| optional additive(s) | | 9.5 |
| Stearic Acid (vegetable) | Palmera B1802G | 2.4 |
| Glycerol Stearate/Stearamide AMP | Ritasynt IP | 1.4 |
| Glycerol Monostearate (vegetal) | Cutina GMS V | 0.6 |
| Cetyl Alcohol | Lanette 16-96 NF | 0.4 |
| PEG-100 Stearate | Myrj 59P/Myrj S-100 | 1.2 |
| Dimethicone 50 CST ($5 \times 10^{-5}$ m$^2$/S) | DC200 Fluid, 50 ($5 \times 10^{-5}$ m$^2$/S) | 1.0 |
| Phenoxyethanol | Phenoxyethanol | 0.5 |
| Cycloalkyl compound 1 | | 0.85 |
| Cycloalkyl compound 3 | | 0.85 |

TABLE 3b

Microbial Test Results

Log 10 cfu/g

| | Pool 1 B. cepacia, P. aeruginosa P. putida | Pool 2 B. cepacia 054 | Pool 3 S. aureus | Pool 4 C. albicans | Pool 5 A. brasiliensis |
|---|---|---|---|---|---|
| Inoculum Level | 6.30 | 6.89 | 7.11 | 5.69 | 5.56 |
| Day 2 | <1.0 | <1.0 | 5.02 | <1.0 | 5.62 |
| Day 7 | <1.0 | <1.0 | <1.0 | <1.0 | 5.01 |
| Day 14 | <1.0 | <1.0 | 2.22 | <1.0 | 5.32 |
| Day 21 | <1.0 | <1.0 | 2.92 | <1.0 | 5.23 |

TABLE 4a

SF Base Control - LM-16024-80 Comparative - no hydroxamic acid

| Ingredient | Trade Name | Weight % |
|---|---|---|
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xanthan Gum | Keltrol CG | 0.3 |
| Potassium Hydroxide (45%) | Potassium Hydroxide | As needed to adjust to a pH of 5 to 8 |
| optional additive(s) | | 9.5 |
| Stearic Acid (vegetable) | Palmera B1802G | 2.35 |
| Glycerol Stearate/Stearamide AMP | Ritasynt IP | 1.4 |
| Glycerol Monostearate (vegetal) | Cutina GMS V | 0.6 |
| Cetyl Alcohol | Lanette 16-96 NF | 0.4 |
| PEG-100 Stearate | Myrj 59P/Myrj S-100 | 1.2 |
| Dimethicone 50 CST ($5 \times 10^{-5}$ $m^2$/S) | DC200 Fluid, 50 CST ($5 \times 10^{-5}$ $m^2$/S) | 1.0 |
| Phenoxyethanol | Phenoxyethanol | 0.5 |
| Cycloalkyl compound 1 | | 0.425 |
| Cycloalkyl compound 3 | | 0.425 |
| Hydroxyacetophenone | SymSave H | 0.25 |

TABLE 4b

Microbial Test Results

Log 10 cfu/g

| | Pool 1 B. cepacia, P. aeruginosa P. putida | Pool 2 B. cepacia 054 | Pool 3 S. aureus | Pool 4 C. albicans | Pool 5 A. brasiliensis |
|---|---|---|---|---|---|
| Inoculum Level | 6.30 | 6.69 | 7.11 | 5.69 | 5.56 |
| Day 2 | <1.0 | <1.0 | 5.03 | 3.0 | 5.41 |
| Day 7 | <1.0 | <1.0 | <1.0 | <1.0 | 4.23 |
| Day 14 | <1.0 | <1.0 | 2.18 | <1.0 | 3.85 |
| Day 21 | <1.0 | <1.0 | 2.46 | <1.0 | 2.26 |

TABLE 5a

SF Control - LM-16024-82 Comparative - No hydroxamic acid and Hydroxyacetophenone

| Ingredient | Trade Name | Weight % |
|---|---|---|
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xanthan Gum | Keltrol CG | 0.3 |
| Potassium Hydroxide (45%) | Potassium Hydroxide | 1.0 |
| optional additive(s) | | 9.5 |
| Sodium Hydroxide (50%) | Sodium Hydroxide | 0.44 |
| Stearic Acid (vegetable) | Palmera B1802G | 2.35 |
| Glycerol Stearate/Stearamide AMP | Ritasynt IP | 1.39 |
| Glycerol Monostearate (vegetal) | Cutina GMS V | 0.65 |

TABLE 5a-continued

SF Control - LM-16024-82 Comparative - No hydroxamic acid and Hydroxyacetophenone

| Ingredient | Trade Name | Weight % |
|---|---|---|
| Cetyl Alcohol | Lanette 16-96 NF | 0.4 |
| PEG-100 Stearate | Myrj 59P/Myrj S-100 | 1.2 |
| Dimethicone 50 CST ($5 \times 10^{-5}$ m²/S) | DC200 Fluid, 50 ($5 \times 10^{-5}$ m²/S) | 1.0 |
| Phenoxyethanol | Phenoxyethanol | 0.5 |
| Cycloalkyl compound 3 | | 0.85 |

TABLE 5b

Microbial Test Results

Log 10 cfu/g

| | Pool 1 B. cepacia, P. aeruginosa P. putida | Pool 2 B. cepacia 054 | Pool 3 S. aureus | Pool 4 C. albicans | Pool 5 A. brasiliensis |
|---|---|---|---|---|---|
| Inoculum Level | 6.53 | 6.61 | 7.09 | 5.80 | 5.41 |
| Day 2 | <1.0 | 2.88 | 5.36 | 4.58 | 5.34 |
| Day 7 | <1.0 | <1.0 | 4.03 | 2.59 | 5.43 |
| Day 14 | <1.0 | <1.0 | 4.84 | 1.3 | 5.41 |
| Day 21 | <1.0 | <1.0 | 4.88 | <1.0 | 5.44 |

TABLE 6A

SF24 Base Control - LM-16024-83-Comparative - No hydroxyacetophenone and hydroxamic acid.

| Ingredient | Trade Name | Weight % |
|---|---|---|
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xanthan Gum | Keltrol CG | 0.3 |
| Potassium Hydroxide (45%) | Potassium Hydroxide | As needed to adjust to a pH of 5 to 8 |
| Stearic Acid (vegetable) | Palmera B1802G | 2.35 |
| Glycerol Stearate/Stearamide AMP | Ritasynt IP | 1.39 |
| Glycerol Monostearate (vegetal) | Cutina GMS V | 0.65 |
| Cetyl Alcohol | Lanette 16-96 NF | 0.4 |
| PEG-100 Stearate | Myrj 59P/Myrj S-100 | 1.2 |
| optional additive(s) | | 9.0 |
| Dimethicone 50 CST ($5 \times 10^{-5}$ m²/S) | DC200 Fluid, 50 CST ($5 \times 10^{-5}$ m²/S) | 1.0 |
| Phenoxyethanol | Phenoxyethanol | 0.5 |
| Cycloalkyl compound 1 | | 0.85 |

TABLE 6B

Microbial Test Results

Log 10 cfu/g

| | Pool 1 B. cepacia, P. aeruginosa P. putida | Pool 2 B. cepacia 054 | Pool 3 S. aureus | Pool 4 C. albicans | Pool 5 A. brasiliensis |
|---|---|---|---|---|---|
| Inoculum Level | 6.43 | 6.89 | 6.98 | 5.61 | 5.49 |
| Day 2 | <1.0 | <1.0 | 5.77 | 4.95 | 5.43 |
| Day 7 | <1.0 | <1.0 | 3.67 | 2.23 | 5.75 |

TABLE 6B-continued

Microbial Test Results

Log 10 cfu/g

| | Pool 1<br>B. cepacia,<br>P. aeruginosa<br>P. putida | Pool 2<br>B. cepacia<br>054 | Pool 3<br>S. aureus | Pool 4<br>C. albicans | Pool 5<br>A. brasiliensis |
|---|---|---|---|---|---|
| Day 14 | <1.0 | <1.0 | 4.73 | <1.0 | 5.43 |
| Day 21 | <1.0 | <1.0 | 4.16 | <1.0 | 4.81 |

TABLE 7a

SPF Control - LM-16024-86 Comparative - Cycloalkyl compound below 0.5 wt. %

| Ingredient | Trade Name | Weight % |
|---|---|---|
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xantham Gum | Keltrol CG | 0.3 |
| Potassium Hydroxide (45%) | Potassium Hydroxide | As needed to adjust to a pH of 5 to 8 |
| Optional additive(s) | | 9.5 |
| Stearic Acid (vegetable) | Palmera B1802G | 2.35 |
| Glycerol Stearate/Stearamide AMP | Ritasynt IP | 1.39 |
| Glycerol Monostearate (vegetal) | Cutina GMS V | 0.65 |
| Cetyl Alcohol | Lanette 16-96 NF | 0.4 |
| PEG-100 Stearate | Myrj 59P/Myrj S-100 | 1.2 |
| Dimethicone 50 CST ($5 \times 10^{-5}$ m$^2$/S) | DC200 Fluid, 50 CST ($5 \times 10^{-5}$ m$^2$/S) | 1.0 |
| Phenoxyethanol | Phenoxyethanol | 0.5 |
| Cycloalkyl compound 1 | | 0.425 |
| Hydroxyacetophenone | SymSave H | 0.25 |
| Caprylhydroxamic Acid/Propanediol | Zeastat | 0.35 |

TABLE 8a

LM-164024-92 Comparative - No Cycloalkyl compound, hydroxyacetophenone and hydroxamic acid

| Ingredient | Trade Name | Weight % |
|---|---|---|
| Water Deionized | | Qs to 100 |
| Disodium EDTA | Dissolvine NA2, Sequestrene NA | 0.05 |
| Carbopol Ultrez 10 | Carpobol Ultrez 10 | 0.4 |
| Glycerin (Porcine Free) | Emery 917 | 4.0 |
| Xanthan Gum | Keltrol CG | 0.3 |
| Potassium Hydroxide (45%) | Potassium Hydroxide | As needed to adjust to a pH of 5 to 8 |
| optional additive(s) | | 9.5 |
| Stearic Acid (vegetable) | Palmera B1802G | 2.35 |
| Glycerol Stearate/Stearamide AMP | Ritasynt IP | 1.4 |
| Glycerol Monostearate (vegetal) | Cutina GMS V | 0.65 |
| Cetyl Alcohol | Lanette 16-96 NF | 0.4 |
| PEG-100 Stearate | Myrj 59P/Myrj S-100 | 1.2 |
| Dimethicone 50 CST ($5 \times 10^{-5}$ m$^2$/S) | DC200 Fluid, 50 ($5 \times 10^{-5}$ m$^2$/S) | 1.0 |
| Phenoxyethanol | Phenoxyethanol | 0.5 |

TABLE 7b

Microbial Test Results

Log 10 cfu/g

| | Pool 1<br>B. cepacia,<br>P. aeruginosa<br>P. putida | Pool 2<br>B. cepacia<br>054 | Pool 3<br>S. aureus | Pool 4<br>C. albicans | Pool 5<br>A. brasiliensis |
|---|---|---|---|---|---|
| Inoculum Level | 6.34 | 6.89 | 6.98 | 5.61 | 5.49 |
| Day 2 | <1.0 | <1.0 | 5.13 | 2.28 | 4.83 |
| Day 7 | <1.0 | <1.0 | 1.04 | <1.0 | 2.52 |
| Day 14 | <1.0 | <1.0 | 2.29 | <1.0 | <1.0 |
| Day 21 | <1.0 | <1.0 | 2.89 | <1.0 | <1.0 |

TABLE 8b

Microbial Test Results

| | Log 10 cfu/g | | | | |
|---|---|---|---|---|---|
| | Pool 1 B. cepacia, P. aeruginosa P. putida | Pool 2 B. cepacia 054 | Pool 3 S. aureus | Pool 4 C. albicans | Pool 5 A. brasiliensis |
| Inoculum Level | 6.13 | 6.81 | 6.97 | 5.28 | 5.36 |
| Day 2 | 4.89 | 4.63 | 5.73 | 5.05 | 5.32 |
| Day 7 | 3.68 | 4.63 | 4.74 | 4.17 | 5.41 |
| Day 14 | 2.62 | 4.43 | 5.46 | 1.3 | 4.88 |
| Day 21 | 2.64 | 4.3 | 6.17 | 1.3 | 4.85 |

The cosmetic compositions shown in tables 1 to 8 were formulated using the following procedure.

1. Weigh out specified quantities of Deionized Water into batching vessel. Begin large prop mixing (~200 RPM) with the IKA-WIERKE instrument (Eurostar Power Control Visc-Stirrer. Mfr. No. IKA 2600000 with L-stirrer attachment) and heat to 75-80° C.
2. Add Disodium Ethylenediaminetetraacetic Acid and Butylated Hydroxytoluene and wait until they are completely dissolved then start adding additional ingredients.
3. Add polymers, glycerine, KOH and mix for 30 minutes.
4. If required, neutralize other water insoluble ingredient(s) separately with Sodium Hydroxide 50% soln. and 10% of the full Water volume for the formulation) to water phase to pH 5 to 7.8 or 8.0 effective to solubilize selected water insoluble ingredients without substantial decomposition or reduction in antimicrobial efficacy in the cosmetic composition.
5. In a separate vessel, add emulsifiers and emollients. Begin light mixing with another IKA-WIERKE instrument (Eurostar Power Control Visc-Stirrer. Mfr. No. IKA 2600000 with Large Prop Mixer attachment) and heat in a water bath to 75-80° C.
6. When temp. of both water and oil phases have reached 80° C. Begin to slowly add the oil phase to water phase.
7. Mix batch when hot with Silverson L4RT-A homogenizer (Model no. L4R) for 1 minute at 3600 rpm.
8. Cool to 40° C. and add Phenoxyethanol, Cyclohexanol compound, Hydroxyacetophenone, and Caprylhydroxamic Acid/Propanediol (Zeastat).
9. Discontinue mixing at 35° C. Q/S batch as necessary with DI Water and mix with cooling sweep until formulation is uniform.

A modified challenge test that complies with the current USP Chapter 51 Antimicrobial Effectiveness Testing and M-3—A Method for Preservative Testing of Water-Miscible Personal Care Products, CTFA Microbiology Guidelines, 2007, was performed. The results are in Table 1b-8b. The tables indicate the log value of the number of viable microorganisms recovered at each sampling time point. The comparative samples failed to meet the 2 log reduction required at Day 7 of the test and for the remainder of the test. The product listed in Table 1 with the anti-microbial composition in accordance with the invention, meets and far exceeds the acceptance criteria for the test method.

The above test methods are standard test methods to determine microbiological efficacy. Personal care products challenge test methods are based on the and M-3—A Method for Preservative Testing of Water-Miscible Personal Care Products, CTFA Microbiology Guidelines, 2007, was performed.

EXAMPLE 3

Tables 9 to 12 illustrate several cosmetically acceptable bases that may be used with the inventive antimicrobial composition.

TABLE 9

Anionic Chassis

| Ingredient | % w/w |
|---|---|
| Water, Deionized | qs to 100 |
| Disodium EDTA | 0.05 |
| Carbopol Ultrez 10 | 0.40 |
| Glycerin (Porcine Free) | 4.0 |
| Xanthan Gum | 0.3 |
| Potassium Hydroxide (45%) | As needed to adjust to a pH of 5 to 8 |
| optional additive(s) | 9.50 |
| Stearic Acid (vegetable) | 2.40 |
| Glycol Stearate/Stearamide AMP | 1.40 |
| Glyceryl Monostearate (vegetal) | 0.70 |
| Cetyl Alcohol | 0.40 |
| PEG-100 Stearate | 1.20 |
| Dimethicone 50 CST ($5 \times 10^{-5}$ m$^2$/S) | 1.0 |

TABLE 10

Cationic Chassis

| Ingredient | % w/w |
|---|---|
| Water, Deionized | qs to 100 |
| Methylparaben | 0.20 |
| Disodium EDTA | 0.05 |
| Sodium Chloride | As needed to adjust to a pH of 5 to 8 |
| Titanium Dioxide | 0.10 |
| Glycerin (Porcine Free) | 16.80 |
| Distearyldimonium Chloride | 4.03 |
| Cetyl Alcohol | 2.88 |
| Steareth-21 | 1.73 |
| Stearyl Stearate | 0.01 |
| Petrolatum G2212 | 0.25 |
| Dimethicone 200/200 CST ($20 \times 10^{-5}$ m$^2$/S) | 1.00 |
| Isopropyl Palmitate | 4.00 |
| Mineral Oil 1000 sus (a) | 2.75 |
| Water, Deionized | 2.00 |
| Tapioca Starch | 0.50 |

(a) calculated centistokes for 1000 SUS at 100 F. and 210 F. are 215.89 cSt ($2.16 \times 10^{-5}$ m$^2$/S) and 214.41 cSt ($2.14 \times 10^{-5}$ m$^2$/S), see section 5.2, ASTM D2161-10.

TABLE 11

Non-Ionic Chassis

| Ingredient | % w/w |
|---|---|
| Water, Deionized | qs to 100 |
| Sodium Cetearyl Sulfate | 0.50 |
| Glycerin (Porcine Free) | 15.00 |
| Aristoflex | 0.35 |
| Disodium EDTA | 0.05 |
| Glyceryl Monostearate | 2.00 |
| Cetearyl Alcohol | 3.00 |
| Stearic Acid veg | 1.00 |
| PEG-100 Stearate | 1.50 |
| Isopropyl Myristate | 2.75 |
| Cetyl Palmitate | 0.50 |
| 12-Hydroxystearic Acid | 0.01 |
| Caprylic/Capric Triglyceride | 3.00 |
| Dimethicone 350 cst ($3.5 \times 10^{-5}$ m$^2$/S) | 3.00 |

TABLE 12

Water/Oil (Invert) Chassis

| Ingredient | % w/w |
|---|---|
| Abil EM 90 (Cetyl PEG/PPG 10/Dimethicone | 2.00 |
| Caprylic/Capric Triglyceride | 5.00 |
| Microcrystalline Wax | 1.00 |
| Dimethicone 200 Fluid 50 cst ($5 \times 10^{-5}$ m$^2$/S) | 3.00 |
| Propylparaben | 0.10 |
| optional additive(s) | 7.50 |
| Cyclomethicone DC 245 | 12.00 |
| Z-Cote HP-1 (Zinc Oxide/Triethoxycaprylsilane) | 5.00 |
| Water, Deionized | qs to 100 |
| Disodium EDTA | 0.05 |
| Sodium Chloride | 0.20 |
| Glycerin (Porcine Free) | 5.00 |
| Optional extract | 0.01 |
| Chamomile Extract | 0.01 |

What is claimed is:

1. A cosmetic composition comprising:
   an antimicrobial composition and a cosmetically acceptable base, wherein the antimicrobial composition comprises:
   a. phenoxyethanol in a concentration of 0.2 to 1.0 wt. %;
   b. caprohydroxamic acid in a concentration of about 0.1 to 1.2 wt. %;
   c. a hydroxyacetophenone selected from the group consisting of 4-hydroxy-acetophenone, 3-hydroxyacetophenone, 2-hydroxyacetophenone and combinations thereof in a concentration of about 0.1% to 1.0 wt. %; and
   d. cycloalkyl compounds

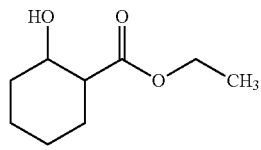
(1)

and

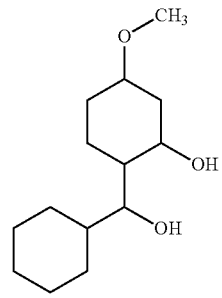
(3)

in a total concentration of about 0.5 to 1.0 wt. %.

2. The cosmetic composition of claim 1, wherein the antimicrobial composition is present in an amount effective to at least inhibit 99% of at least one viable microorganism from re-growth using the modified challenge test at day 21 and further wherein the microrganism is selected from *B.cepacia, P.aeruginosa, P.putida, S.aureus, C.albicans* and *A.brasiliensis* or any combination thereof.

3. The cosmetic composition of claim 1 further comprising isothiazolinone antimicrobial compounds; wherein total isothiazolinone antimicrobial compounds are present at a maximum level of 0.15 wt. % as a total amount based on the weight of the cosmetic composition.

4. The cosmetic composition according to claim 1, wherein the composition is a medicament.

5. The cosmetic composition according to claim 4 wherein the composition is an antimicrobial composition.

6. The cosmetic composition of claim 1, wherein the antimicrobial composition is present in an amount effective to at least inhibit 99% of viable microorganism *B.cepacia* from re-growth using the modified challenge test at day 21.

* * * * *